United States Patent [19]

Wallace

[11] Patent Number: Plant 7,041

[45] Date of Patent: Sep. 26, 1989

[54] CAROLINA CHESTNUT

[76] Inventor: Robert D. Wallace, Rte. 1, Box 341, Alachua, Fla. 32615

[21] Appl. No.: 206,877

[22] Filed: Jun. 13, 1988

[51] Int. Cl.[4] ..... A01H 5/00

[52] U.S. Cl. ..... Plt./30

[58] Field of Search ..... Plt. 30

*Primary Examiner*—James R. Feyrer

[57] ABSTRACT

A large, vigorous hybrid chestnut tree, having an upright growth form with broadly spreading branches and a rounded crown, and abundant, lustrous foliage of large elliptical leaves with slightly dentate margins, and strongly scented flowers appearing in spring after leafing out; the tree being a regular and very prolific bearer of large, dark colored and very sweet, easy-to-peel nuts, the nuts ripening and falling free from the burr in mid September to the first of October; the tree also exhibiting a very high inherent resistance to the chestnut bark blight (*Endothia parasitica*), not showing a single instance of blight infection in 15 years of growth in the orchard.

1 Drawing Sheet

ORIGIN OF THE VARIETY

The present variety is a specially selected seedling from second generation American×Chinese hybrid chestnuts (unpatented) growing in the Chestnut Hill Nursery Orchards in Alachua, Fla. These second generation trees were produced from a cross made by Dr. Robert T. Dunstan, between flowering grafts of an uninfected native American chestnut (unpatented) found in a grove of dead and dying chestnuts, and a tree grafted to 3 USDA released varieties of Chinese chestnut, Kuling, Meiling, and Nanking (all unpatented), in 1953 in North Carolina. Seedlings from this cross were and then backcrossed to the American parent tree. The second generation was planted out in the Chestnut Hill orchard where they continue to grow in excellent condition. The present variety was produced by the same method as the Revival Chestnut (U.S. Plant Pat. No. 5,537) and Heritage Chestnut (U.S. Plant Pat. No. 6,674), where nuts from the second generation trees bearing the largest and sweetest nuts were planted. These seedlings (third generation) were grown in the nursery and then transplanted to the orchard. The present variety is a single third generation seedling tree, exhibiting excellent qualities in nut size, taste and production that I have determined to be novel and distinct.

ASEXUAL REPRODUCTION OF THE VARIETY

The present variety having outstanding characteristics, was asexually reproduced by myself by grafting on to Chinese chestnut rootstocks (unpatented). In maturity, all such reproductions run true to the original tree in all respects.

SUMMARY OF THE VARIETY

The present variety of chestnut tree is of large size, vigorous in growth, attaining a height of over 30′ in 15 years, and with an upright bole and broadly spreading branches (over 15 feet in diameter at 15 years of age) and a rounded crown, having abundant, lustrous foliage with large, elliptical leaves with only a slightly dentate margin, flowering late but profusely after leafing out; the tree, bearing only several years after graft placement and regularly every year, is a very productive bearer of very large dark brown nuts, 2–3 per burr, the nuts ripening and falling free from the burrs in mid-September. The pellicle is easily released from the kernel, and the meat is a yellowish cream color and very sweet to taste. The present variety can be distinguished from the Revival Chestnut (U.S. Plant Pat. No. 5,537) by its larger and more spreading growth form, its elliptical leaves with a slightly dentate margin and its larger, sweeter and much darker colored nuts, and can be distinguished from Heritage Chestnut (U.S. Plant Pat. No. 6,674) by its shorter stature, much more spreading crown, much less deeply dentate leaves, and much larger, darker colored, and rounded instead of pointed nuts.

The present variety is characterized by rapid growth and heavy bearing, and is capable of growing and producing well in a wide variety of regions throughout the original range of the American chestnut, from southern New England to the Gulf Coast and west to the Mississippi. The present variety is also importantly characterized by a high degree of genetic resistance to the chestnut blight (*Endothia parasitica*), having never been infected with the blight in over 15 years of growth in the orchard. The present variety has the good form and blight resistance in combination with the important characteristics of large, sweet and easy-to-peel nuts that make it an outstanding tree for both landscaping and commercial orchard production of excellent quality chestnuts.

BRIEF DESCRIPTION OF THE DRAWING

The drawing is an illustration, by photographic reproduction in color, of a twig with leaves and burrs and nuts out of the burrs.

DESCRIPTION OF THE VARIETY

The botanical details of this new and distinct variety of chestnut tree—with color definitions (except those in common color terms) referenced to *Maerz and Paul Dictionary of Color*—are as follows:

Tree:

*Size (at maturity).*—Large, ultimately approaching a height of 60–70 feet and a spread of 30 feet or more.

*Vigor.*—Vigorous, attaining a height of 30 feet and a spread of 15 feet within 15 years at its location near Alachua, Fla.

Trunk:

*Form.*—Upright bole, with spreading branches and a rounded crown.

*Texture.*—Smooth on young trees and rough in older wood.

*Color of bark.*—Gray (14-C-2).

Branches:

*Form.*—Strong.

*Texture.*—Smooth.

*Lenticels.*—Few, small.

*Branching habit.*—Broadly spreading, with the first scaffold branches starting about 5 feet above the ground, and typical lower crotch angles approaching 90 degrees.

*Color.*—New wood: Brown (14-L-9). Mature wood: Gray (14-C-2).

Foliage:

*Quantity.*—Abundant.

*Density.*—Dense.

Leaves:

*Size.*—Large. Average length — 7–9" (including petiole). Average width — 2–2½".

*Shape.*—Elliptical with acute tip and rounded base.

*Thickness.*—Thick.

*Texture.*—Smooth.

*Margin.*—Slightly dentate.

*Petiole.*—Length: Medium. Thickness: Medium.

*Color.*—Top side — Lustrous dark green (30-L-12). Under side — Lighter green (21-I-5).

Bloom:

*Amount of bloom.*—Heavy.

*Color.*—Yellowish white (17-B-1).

*Blooming period.*—Late. After leaf out in May.

*Age at which tree starts flowering.*—Early; 2–3 years after graft placement.

Crop:

*Bearing.*—Regular (yearly) bearer.

*Productivity.*—Prolific.

*Ripening period.*—Short. September 10–September 25.

*Distribution of nuts on tree.*—Well distributed.

*Tenacity.*—Nuts easily released for harvesting.

Hull:

*Description.*—Rounded burr with dense, short spines.

*Size.*—3–4" in diameter.

*Number of nuts.*—2–3 per burr.

*Dehiscence.*—Splits easily when still on tree.

*Color.*—Brown (15-A-12).

Nut:

*Size.*—Very large. Average size — 1¼"×1¼" thick. Average weight — 20–25 nuts per pound.

*Form.*—Broad and ovoid on one side, flat on other side.

*Blossom end.*—Rounded tip.

*Basal end.*—Flattened.

*Color.*—Very dark brown (56-L-1).

*Shell.*—Thin.

*Hardiness of shell.*—Firm.

*Texture of shell.*—Smooth.

*Percentage of kernel to nut.*—Very high (95%).

Kernel:

*Size.*—Almost as large as nut size.

*Form.*—Same as nut shape.

*Pellicle.*—Thin, very easily removed, even fresh.

*Flavor.*—Very sweet.

*Color.*—Yellowish cream (10-C-1).

Resistance to insects: No unusual susceptibilities noted.

Resistance to disease: High genetic resistance to chestnut bark fungus (*Endothia parasitica*), no other susceptibilities to any other disease.

The chestnut tree and its nuts herein described may vary in slight detail due to climatic and soil conditions under which the variety may be grown; the present description being of the variety as grown in Alachua, Fla.

I claim:

1. A new and distinct variety of hybrid chestnut tree, substantially as illustrated and described, which is of large size, vigorous in growth, upright in form with broadly spreading branches and a rounded crown, with abundant foliage and large, lustrous, elliptical leaves with slightly dentate margins and late flowering; the tree being a regular and prolific bearer of large, dark-colored and very sweet nuts that ripen and fall free from the burrs in early to late September; the trees being especially characterized by having the combination of good tree form and large, sweet and easy-to-peel nuts with a high genetic resistance to the chestnut bark blight that make it a valuable tree for both landscaping and commercial nut production of high quality chestnuts.

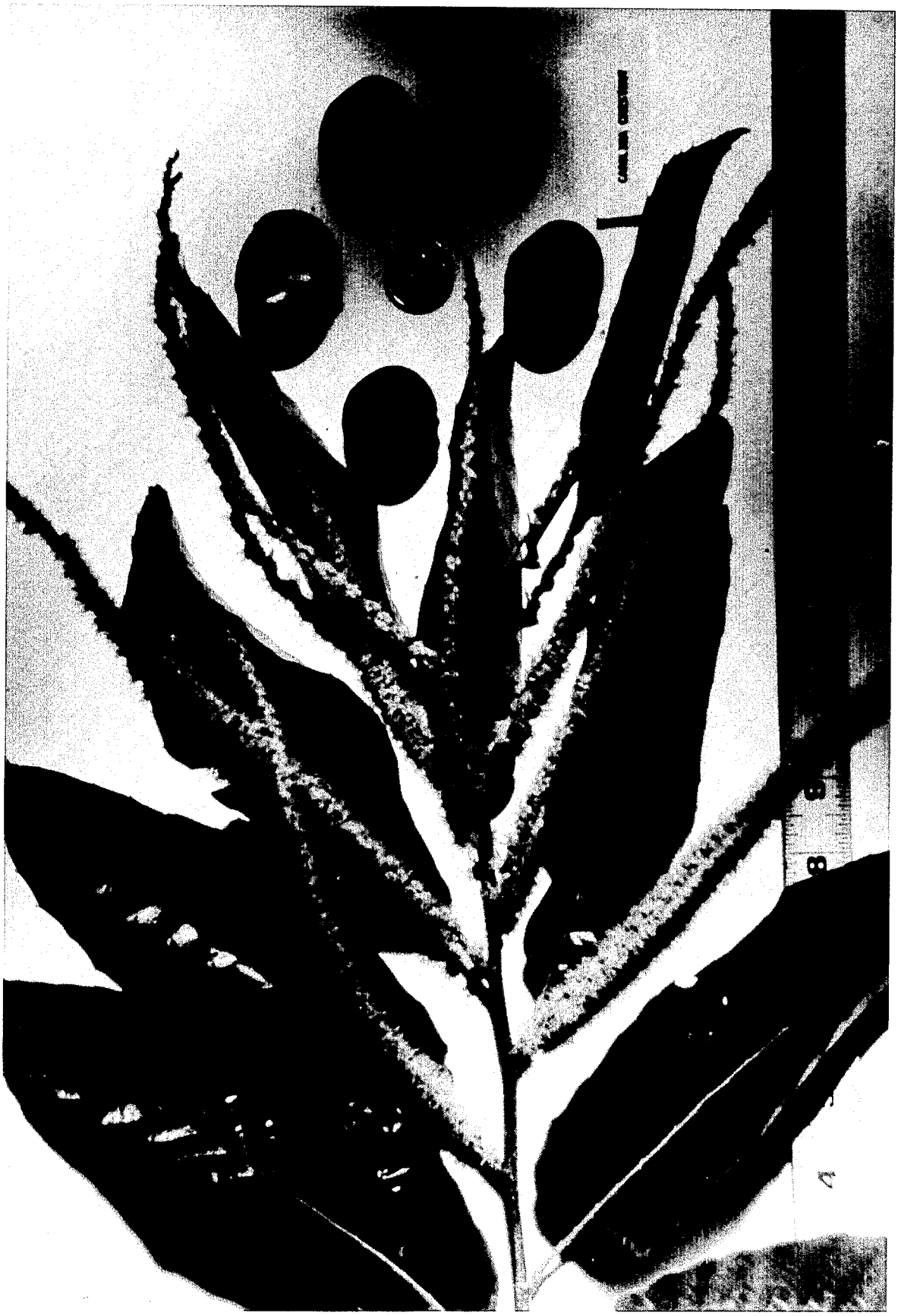

* * * * *